United States Patent
Kirovski et al.

(10) Patent No.: US 8,452,541 B2
(45) Date of Patent: May 28, 2013

(54) VACCINE DESIGN METHODOLOGY

(75) Inventors: Darko Kirovski, Kirkland, WA (US); David E. Heckerman, Bellevue, WA (US); Nebojsa Jojic, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 1710 days.

(21) Appl. No.: 11/764,402

(22) Filed: Jun. 18, 2007

(65) Prior Publication Data

US 2008/0312095 A1 Dec. 18, 2008

(51) Int. Cl.
*G01N 33/48* (2006.01)
*G06F 19/00* (2011.01)

(52) U.S. Cl.
USPC .................................. 702/19; 703/11; 702/22

(58) Field of Classification Search
None
See application file for complete search history.

(56) References Cited

U.S. PATENT DOCUMENTS

| | | | |
|---|---|---|---|
| 4,886,782 | A | 12/1989 | Good et al. |
| 7,128,915 | B2 | 10/2006 | Hernandez et al. |
| 2003/0134335 | A1 | 7/2003 | Warmerdam et al. |
| 2004/0197343 | A1 | 10/2004 | Dubensky et al. |
| 2006/0095241 | A1 | 5/2006 | Jojic et al. |
| 2006/0190226 | A1 | 8/2006 | Jojic et al. |
| 2006/0233820 | A1 | 10/2006 | Zagury et al. |
| 2006/0257865 | A1 | 11/2006 | Mallal |
| 2006/0257944 | A1 | 11/2006 | Fridman et al. |

FOREIGN PATENT DOCUMENTS

WO 02083714 A2 10/2002

OTHER PUBLICATIONS

Beerenwinkel et al. (Journal of Computational Biology, vol. 12, No. 6, p. 584-598, 2005).*
Hanke et al. (Nature Medicine, vol. 6, No. 9, p. 951-955, 2000).*
Tong et al. (Briefings in Bioinformatics, vol. 8, No. 2, p. 96-108, 2006).*
Wu et al. (Information Processing Letters, vol. 69, p. 63-67, 1999).*
Vanetik et al. (Second IEEE International Conference on Data Mining (ICDM'02), p. 458-465, 2002).*
Govinidan et al. (Proc IEEE Infocom., vol. 3, pp. 1371-1380, 2000).*
Pai et al. (Nucleic Acids Research, vol. 34, p. w198-w201, 2006).*
International Search Report and Written Opinion for PCT Application No. PCT/US2008/067193 completed and mailed Feb. 20, 2009, 11 pages.
Livingston, et al. "Optimization of Epitope Enhaced Immunogenicity of Multiepitope DNA Vaccines" (Sep. 19, 2001) Vaccine. vol. 19, No. 32, pp. 4652-4600.
Jojic, et al. "Using 'Epitomes' To Model Genetic Diversity:Rational Design of HIV Vaccine Cocktails", http://books.nips.cc/papers/files/nips18/NIPS2005_0759.pdf, last viewed Feb. 13, 2007, 8 pages.
Florea, et al. "Epitope Prediction Algorithms for Peptide-based Vaccine Design", Proceedings of the Computational Systmes Bioinformatics, http://conferences.computer.org/Bioinformatics/CSB2003/PDF/key_invited/007_invited-1strail.pdf, last viewed Feb. 13, 2007, 10 pages.
Harish, et al. "DyNAVacS: An Integrative Tool for Optimized DNA Vaccine Design", PubMed Central, http://www.pubmedcentral.nih.gov/articlerender.fcgi?artid=1538838, Jul. 1, 2006, 7 pages.
Florea, et al. "Epitope Prediction Algorithms for Peptide based Vaccine Design", http://portal.acm.org/citation.cfm?id=937976.938017&coll=GUIDE&dl=ACM&CFID=15151515&CFTOKEN=6184618, last viewed Feb. 13, 2007, 2 pages, Abstract Only.
Fischer, et al. "Polyvalent vaccines for optimal coverage of potential T-cell epitopes in global HIV-1 variant," Nature Medicine, 2007, 7 pages, vol. 13, No. 1, p. 100-106.
McMichael, et al. "The quest for an AIDS vaccine: Is the CD8+ T-cell approach feasible?", Nature Reviews Immunology, 2002, 8 pages, vol. 2, p. 283-291.
Jojic et al. "Using epitomes to model genetic diversity: Rational design of HIV vaccine," Advances in Neural Information Processing Systems, MIT Press, 2005, 8 pages, Cambridge, MA.
McKinney et al. "Recognition of cariant HIV-1 epitopes from diverse viral subtypes by vaccine induced CTL," Journal of Immunology, 2004, 10 pages, vol. 173, p. 1941-1950.
Heckerman, et al. "Leveraging information across HLA alleles/supertypes improves epitope prediction," Recomb, 2006, 13 pages, p. 296-308.
Moore, et al. "Evidence of HIV-1 adaptation to HLA-restricted immune responses at a population level," Science, 2002, 6 pages, vol. 296, 1439-1443.
Rodriguez, et al. "Immunodominance in virus-induced CD8(+) T-cell responses is dramatically modified by DNA immunization and is regulated by gamma interferon," Journal of Virology, 2002, 9 pages, vol. 76, No. 9, p. 4251-4259.
DeGroot et al. "HIV vaccine development by computer assisted design: The GAIA vaccine," Vaccine, 2005, 13 pages, vol. 23, p. 2136-2148.
Draenert et al. "Immune selection for altered antigen processing leads to cytotoxic T-lymphocyte escape in chronic HIV-1 infection," Journal of Experimental Medicine, 2004, 11 pages, vol. 199, p. 905-915.

(Continued)

Primary Examiner — Eric S DeJong
(74) Attorney, Agent, or Firm — Lee & Hayes, PLLC

(57) ABSTRACT

Systems and methodologies for efficient vaccine design are disclosed herein. A methodology for efficient vaccine design in accordance with one or more embodiments disclosed herein may be operable to receive a graph having vertices corresponding to epitope sequences present in the pathogen population, weights for respective vertices corresponding to respective frequencies with which corresponding epitope sequences appear in the pathogen population, and directed edges that connect vertices that correspond to overlapping epitope sequences. Such a methodology may also be operable to determine a candidate vaccine sequence of overlapping epitope sequences by identifying a path though the graph corresponding to a series of connected vertices and directed edges that maximizes the total weight of the vertices in the path for a desired vaccine sequence length.

20 Claims, 11 Drawing Sheets

OTHER PUBLICATIONS

Milicic et al. "CD8+ T-cell epitope-flanking mutations disrupt proteasomal processing of HIV-1 Nef." Journal of Immunology, 2005, 9 pages, vol. 175, p. 4618-4626.

Crescenzi, et al., "A compendium of NP optimization problems", Retrieved on Sep. 17, 2010 at <<http://www.nada.kth.se/~viggo/problemlist/>>, 2 pages.

F. Glover et al., "Tabu Search", Kluwer, 1997, 18 pages.

Kirkpatrick, et al., "Optimization by Simulated Annealing", Science, vol. 220, No. 4598, pp. 671-680, 1983.

Kirovski, et al., "Combinatorics of The Vaccine Design Problem: Definition and An Algorithm", Technical Report MSR-TR-2007-148, Microsoft Reaserch, Nov. 2007, 11 pages.

Nickle, et al., "Coping with viral diversity in HIV vaccine design", PLoS, vol. 3, No. 4, p. e75, DOI:10.1371/journal.pcbi.0030075, 2007, 14 pages.

Waldspurger et al., "Lottery Scheduling: Flexible Proportional-Share Resource Management", USENIX Symposium on Operating Systems Design and Implementation, 1994, 11 pages.

* cited by examiner

SEQUENCE LISTING

<160> NUMBER OF SEQ ID NOS: 14

<210> SEQ ID NO 1
<211> LENGTH: 50
<212> TYPE: PRT
<213> ORGANISM: Artificial Sequence
<220> FEATURE:
<223> OTHER INFORMATION: Synthetic example used for illustration
      purposes

<400> SEQUENCE: 1

```
Met Leu Ile Cys Lys Arg Asp Cys Ile Ala Glu Leu Asp Arg Gln Lys
1               5                   10                  15

Lys Met Met Asn Ile His Glu Cys Ile Thr Ala Phe Trp Phe Ser Lys
            20                  25                  30

Asp Pro Val Glu Pro Asp Pro Thr Trp Lys Gly Trp Trp Met Thr Glu
        35                  40                  45

His Gln
    50
```

<210> SEQ ID NO 2
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 2

```
Leu Ile Cys Lys Arg Asp Cys Ile Ala Glu Leu Asp Met Asn Ile His
1               5                   10                  15

Glu Cys Ile Thr Ala Phe Pro Asp Pro Thr Trp Lys Gly Trp Trp Met
            20                  25                  30

Thr Glu His Gln Ala Met Met Gln Trp
        35                  40
```

<210> SEQ ID NO 3
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 3

```
Ala Phe Leu Ser Lys Phe Gly Tyr Tyr Cys Asn Ile His Glu Cys Ile
1               5                   10                  15

Thr Ala Phe Trp Phe Ser Asn Glu Asn Glu Leu Lys Asp Pro Val Glu
            20                  25                  30

Pro Asp Pro Thr Trp Lys Gly Trp Glu
        35                  40
```

<210> SEQ ID NO 4
<211> LENGTH: 43
<212> TYPE: PRT
<213> ORGANISM: Artificial Sequence
<220> FEATURE:
<223> OTHER INFORMATION: Synthetic example used for illustration
      purposes

<400> SEQUENCE: 4

```
Cys Lys Arg Asp Cys Ile Ala Glu Leu Asp Arg Gln Lys Ile His Glu
1               5                   10                  15
```

```
Cys Ile Thr Ala Phe Trp Phe Val Glu Pro Asp Pro Thr Trp Lys Gly
            20                  25                  30

Trp Trp Met Thr Thr Glu His Gln Trp Met Thr
            35                  40
```

<210> SEQ ID NO 5
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 5

```
Glu Asn Arg Glu Ala Lys Lys Met Met Asn Ile His Glu Cys Ile Thr
1               5                   10                  15

Ala Phe Cys Phe Ser Lys Asp Pro Val Glu Pro Asp Pro Thr Trp Lys
            20                  25                  30

Gly Ser His Gly Trp Trp Met Thr Glu
            35                  40
```

<210> SEQ ID NO 6
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 6

```
Met Val Asn Asn Glu Asp Glu Val Glu Thr Asn Ile Trp Ser Lys Lys
1               5                   10                  15

Met Met Asn Ile His Glu Cys Ile Thr Ala Phe Cys Arg Phe Ser Lys
            20                  25                  30

Asp Pro Val Glu Pro Asp Pro Thr Trp
            35                  40
```

<210> SEQ ID NO 7
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 7

```
Met Thr Met His Asp Cys Ile Ala Glu Leu Asp Arg Gln Lys Lys Met
1               5                   10                  15

Met Ile Asp Arg Cys Ile Thr Ala Phe Trp Phe Ser Lys Asp Pro His
            20                  25                  30

Val Glu Pro Asp Pro Thr Trp Lys Gly
            35                  40
```

<210> SEQ ID NO 8
<211> LENGTH: 42
<212> TYPE: PRT
<213> ORGANISM: Artificial Sequence
<220> FEATURE:
<223> OTHER INFORMATION: Synthetic example used for illustration
      purposes

<400> SEQUENCE: 8

```
Phe Arg Gln Tyr Ser Cys Lys Lys Arg Asp Cys Ile Ala Glu Leu Asp
1               5                   10                  15
```

```
Arg Gln Lys Lys Met Met Ala Met Asn Ile His Glu Cys Ile Thr Ala
            20                  25                  30

Phe Trp Phe Ser Lys Asp Phe Ile Leu Ala
            35                  40

<210> SEQ ID NO 9
<211> LENGTH: 42
<212> TYPE: PRT
<213> ORGANISM: Artificial Sequence
<220> FEATURE:
<223> OTHER INFORMATION: Synthetic example used for illustration
      purposes

<400> SEQUENCE: 9

Cys Glu Ile Ala Glu Leu Asp Arg Gln Lys Lys Met Met Asn Gln Trp
1               5                   10                  15

Phe Ser Lys Asp Pro Val Glu Pro Asp Pro Thr Ala Lys Gly Trp Trp
            20                  25                  30

Met Thr Glu His Gln His Gln Thr Ile
            35                  40

<210> SEQ ID NO 10
<211> LENGTH: 42
<212> TYPE: PRT
<213> ORGANISM: Artificial Sequence
<220> FEATURE:
<223> OTHER INFORMATION: Synthetic example used for illustration
      purposes

<400> SEQUENCE: 10

Asn Ile Asn Met Phe Trp Phe Ser Lys Asp Pro Val Glu Pro Asp Pro
1               5                   10                  15

Thr Trp Asp Gln His Gly Pro Leu Met Lys Gly Trp Trp Met Thr Glu
            20                  25                  30

His Gln Thr Thr Glu His Gln Glu His Gln
            35                  40

<210> SEQ ID NO 11
<211> LENGTH: 43
<212> TYPE: PRT
<213> ORGANISM: Artificial Sequence
<220> FEATURE:
<223> OTHER INFORMATION: Synthetic example used for illustration
      purposes

<400> SEQUENCE: 11

Cys Lys Arg Asp Cys Ile Ala Glu Leu Asp Arg Gln Lys Lys Glu Glu
1               5                   10                  15

Val Ile Pro Asn Ile His Glu Cys Ile Thr Ala Phe Trp Phe Ser Lys
            20                  25                  30

Asp Pro Val Val Glu Pro Asp Pro Thr Trp Lys
            35                  40

<210> SEQ ID NO 12
<211> LENGTH: 41
<212> TYPE: PRT
<213> ORGANISM: Artificial Sequence
<220> FEATURE:
<223> OTHER INFORMATION: Synthetic example used for illustration
      purposes

<400> SEQUENCE: 12

Gln Lys Lys Met Met Asn Ile His Glu Cys Ile Thr Ala Trp Phe Ser
1               5                   10                  15
```

```
Lys Asp Pro Val Glu Pro Asp Pro Thr Trp Gly Trp Trp Met Thr Glu
            20                  25                  30

His Gln Gln Ile Arg Phe Ala Ile Gln
        35                  40

<210> SEQ ID NO 13
<211> LENGTH: 42
<212> TYPE: PRT
<213> ORGANISM: Artificial Sequence
<220> FEATURE:
<223> OTHER INFORMATION: Synthetic example used for illustration
      purposes

<400> SEQUENCE: 13

Lys Arg Asp Cys Ile Ala Glu Leu Asp Arg Gln Lys Lys Met Met Ala
1               5                   10                  15

Phe Trp Phe Ser Lys Asp Pro Val Glu Pro Asp Pro Thr Leu Phe Ile
            20                  25                  30

Trp Lys Gly Trp Trp Met Thr Glu His Gln
        35                  40

<210> SEQ ID NO 14
<211> LENGTH: 27
<212> TYPE: PRT
<213> ORGANISM: Artifical Sequence
<220> FEATURE:
<223> OTHER INFORMATION: Synthetic example used for illustration
      purposes

<400> SEQUENCE: 14

Pro Gly Val Arg Tyr Pro Leu Thr Phe Gly Trp Pro Ala Ile Arg Glu
1               5                   10                  15

Arg Met Arg Arg Ala Glu Pro Ala Ala Asp Gly
            20                  25
```

VACCINE DESIGN METHODOLOGY

TECHNICAL FIELD

The subject invention relates generally to vaccine design, and more particularly to techniques for optimizing vaccine coverage over a predetermined vaccine length.

BACKGROUND OF THE INVENTION

The ability of vaccines to protect the public from disease has made vaccines an integral and vitally important part of today's society. Traditionally, many vaccines are produced directly from samples of a pathogen by either weakening or completely eliminating the ability of the pathogen to cause disease. However, this traditional vaccine production approach is of only limited effectiveness against diseases such as influenza that are caused by pathogens that frequently mutate. Moreover, some pathogens, such as the human immunodeficiency virus (HIV), mutate at such a rate that traditional vaccine production approaches are rendered substantially ineffective.

Research in the fields of immunology and biotechnology has attempted to mitigate the problems associated with vaccine design for rapidly mutating pathogens such as HIV by providing a computational approach to vaccine design. Most of the research in computational vaccine design has focused on cocktail approaches, wherein a series of nucleotides or amino acids corresponding to portions of a collection of similar virus strains or other pathogens is synthesized to enable the human immune system to create antibodies for the pathogens represented by the synthesized sequence. However, vaccines created from these cocktail approaches are typically significantly large in size. As a result, vaccines created using cocktail approaches may be difficult to deliver, expensive to produce, and more likely to cause an autoimmune reaction in a recipient.

In view of at least the above, there exists a need in the art for an efficient technique for constructing an effective vaccine while minimizing the required size of the vaccine.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

Systems and methodologies for vaccine design in accordance with various embodiments disclosed herein can represent a pathogen population having a wide genetic diversity by synthesizing major histocompatibility complex class I (MHC-I) epitopes obtained from the pathogen population such that the MHC-I epitopes overlap. By doing so, a generated vaccine can be shorter than a vaccine with no overlap, thereby mitigating the difficulties associated with the larger size of such vaccines, while providing similar coverage to a vaccine with no overlap. In addition, the generated vaccine may be further improved by weighting the epitopes according to their frequency in the pathogen population and constructing the vaccine such that the combined weights of all epitopes in the vaccine are maximized over a predetermined vaccine length.

In accordance with one embodiment disclosed herein, a vaccine may be constructed based on MHC-I epitopes and/or other known or potential epitope sequences obtained from a pathogen population by first constructing a graph based on the epitopes. The graph may be constructed such that each vertex in the graph corresponds to an epitope. Each vertex may then be weighted according to, among other factors, the frequency of the corresponding epitope in the pathogen population. Each vertex may also be connected to other vertices that correspond to other epitopes in the pathogen population that the epitope overlaps. A vaccine may then be generated that corresponds to the maximum-weight length-constrained path (MLP) through the graph. To reduce the complexity associated with finding the MLP, a probabilistic least-constraining most-constrained algorithm may be employed. Under such an algorithm, a preset number of random paths may be determined using a lottery-scheduling-based search strategy and a set of computationally-inexpensive cost functions, and a determined path that maximizes the cumulative vertex weight over a predetermined vaccine length may then be utilized.

To the accomplishment of the foregoing and related ends, the invention then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed and the subject invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

FIG. 1 is a block diagram of a system that facilitates vaccine design in accordance with an aspect of the present invention.

FIGS. 8A-8B illustrate performance data for an example vaccine design algorithm in accordance with an aspect of the present invention.

DETAILED DESCRIPTION OF THE INVENTION

Figure 2:
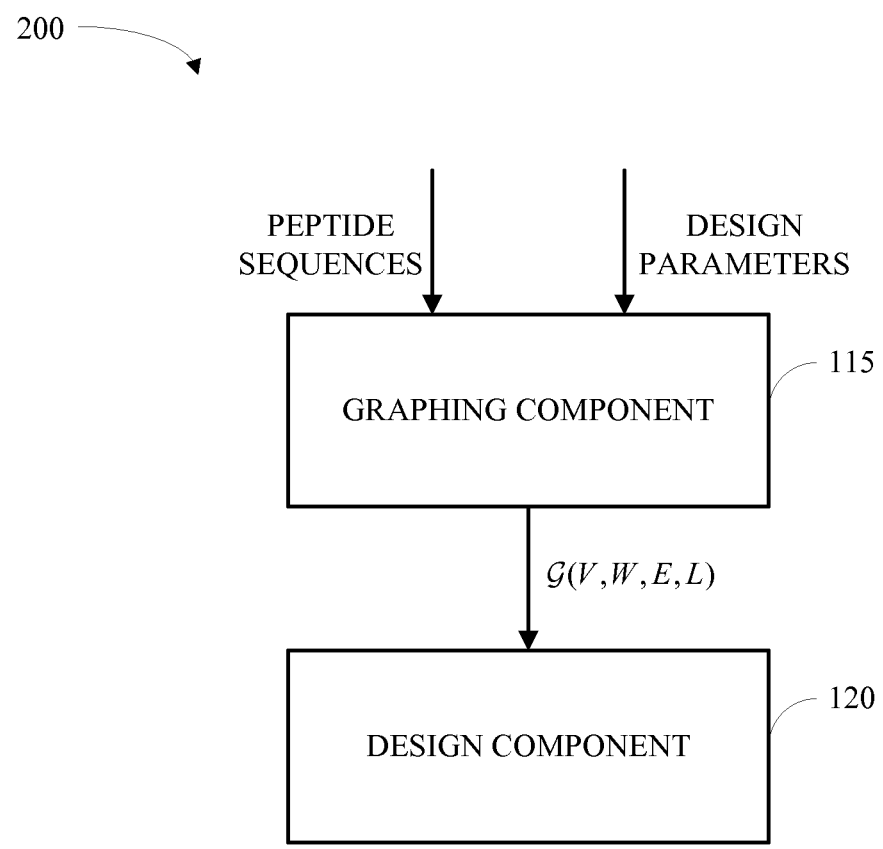
FIG. 2 is a block diagram of a system that facilitates vaccine design in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "system," "algorithm," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. The components may communicate via local and/or remote processes such as in accordance with a signal having one or more data packets (e.g., data from one component interacting with another component in a local system, distributed system, and/or across a network such as the Internet with other systems via the signal).

Thus, the embodiments disclosed herein, or certain aspects or portions thereof, may take the form of program code (i.e., instructions) embodied in tangible media, such as floppy diskettes, CD-ROMs, hard drives, or any other machine-readable storage medium. When the program code is loaded into and executed by a machine, such as a computer, the machine becomes an apparatus for practicing the invention. In the case of program code execution on programmable computers, the computing device generally includes a processor, a storage medium readable by the processor (including volatile and non-volatile memory and/or storage elements), at least one input device, and at least one output device.

Figure 1:
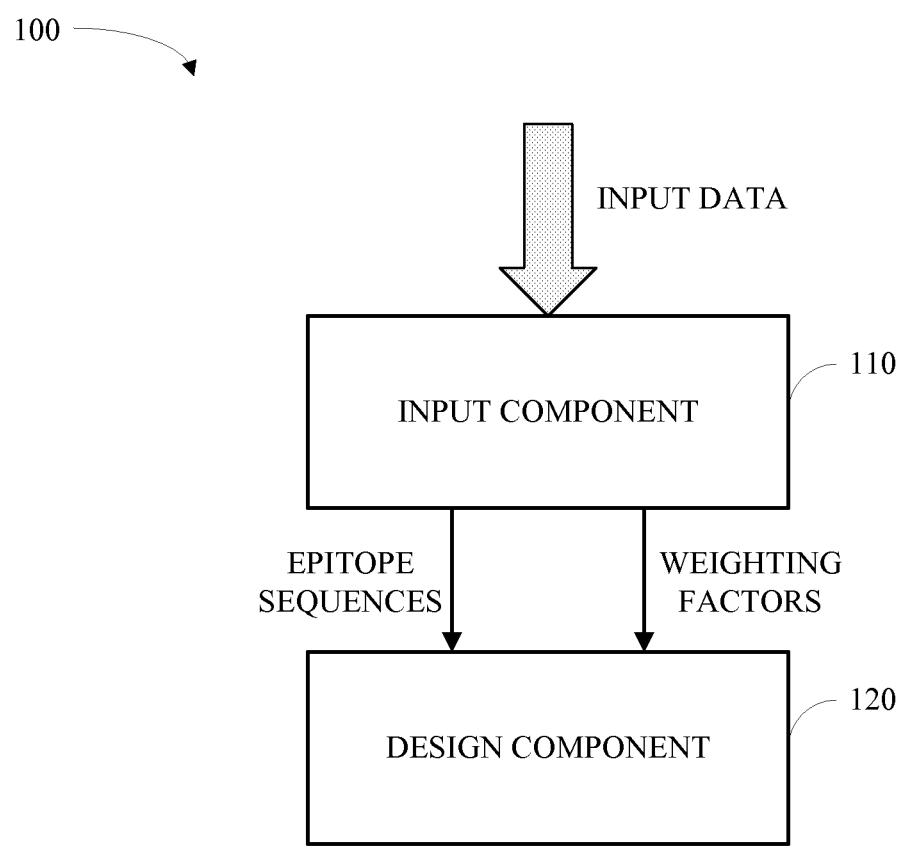

Referring now to the drawings, FIG. 1 illustrates a block diagram of a system 100 that facilitates vaccine design in accordance with an aspect of the present invention. In one example, input data can be provided to the system 100 via an input component 110. The input data may correspond to, for example, a set of amino acid sequences P that corresponds to a set of viral strains in a given pathogen population. The pathogen population represented by the input data may be composed of like strains, such as HIV strains. Alternatively, the pathogen population may include multiple distinct classifications of strains.

In one example, the input component 110 can process the set of viral sequences P present in the input data into a set of epitope sequences. By way of a specific, non-limiting example, the input component 110 may identify unique major histocompatibility complex class I (MHC-I) epitopes present in the viral sequences, i.e., peptide sequences that are presented with MHC-I molecules on the cell surface and trigger T-cell recognition and antibody creation. The input component 110 may identify MHC-I epitopes by comparing each viral sequence to a known list of MHC-I epitopes and/or by any other suitable means. By way of an additional non-limiting example, the input component 110 may identify unique potential epitope sequences present in the viral sequences based on characteristics of the amino acids that constitute the viral sequences, the position of a potential epitope sequence in a viral sequence, and/or other appropriate factors. For example, the input component 110 can divide each viral sequence present in the input data into uniform subsequences of amino acids and designate each subsequence as a potential epitope sequence. As an example, each subsequence can include 10 amino acids; however, it should be appreciated that the viral sequences may be divided into uniform subsequences of any size.

In another example, the input component 110 can also create a set of weighting factors for the determined epitope sequences. Each epitope sequence may then be associated with one or more weighting factors. By way of non-limiting example, weighting factors associated with an epitope sequence may correspond to the number of viral sequences in the input data that include the associated epitope sequence, the probability that the associated epitope sequence is a MHC-I epitope, and/or the expressiveness of the associated epitope sequence in a vaccine. In addition, the weighting factors associated with an epitope sequence may reflect potential cross-reactivity between the associated epitope sequence and other epitope sequences in a vaccine, i.e., the probability that a T-cell trained to recognize the associated epitope will attach the other epitopes. Further, the weighting factors associated with an epitope may correspond to the potential impact on the effectiveness of the associated epitope in a given vaccine strain due to flanking regions of the vaccine strain as well as any other suitable factors.

In accordance with one aspect, the system 100 further includes a design component 120 that facilitates the design of a vaccine for the viral sequences represented by the input data. The design component may design the vaccine based on the epitope sequences and weighting factors received from the input component 110. In one example, the vaccine is designed as a T-cell vaccine by constructing a candidate vaccine strain. The candidate vaccine strain may be composed as an amino acid sequence and may include (or "cover") some or all of the epitope sequences provided by the input component 110.

In another example, the design component 120 can construct a candidate vaccine strain such that epitope sequences covered by the vaccine strain overlap. By doing so, a vaccine strain generated by the design component 120 can provide the epitope coverage of a candidate vaccine strain constructed utilizing traditional cocktail approaches to vaccine design while being significantly smaller in size than such a strain. Thus, candidate vaccine strains constructed by the design component 120 may enjoy benefits such as increased ease of creation, increased ease of administration, reduced cost, reduced probability of an autoimmune reaction, and/or other benefits. As used generally herein, a candidate vaccine strain generated by the design component 120 may be referred to as an "epitome" due to the fact that such a vaccine strain can epitomize the epitope sequences that go into its creation.

The design component may also utilize the epitope sequences and weighting factors received by the input component 110 to execute an efficient algorithm for the construction of a candidate vaccine strain. Under an example of such an algorithm, the design component 120 can determine an amino acid sequence S corresponding to a candidate vaccine strain that covers the most epitope sequences in the viral sequences given as input data to the input component 110. An epitope sequence can be said to be covered, for example, when it is a substring of the candidate vaccine sequence S. In order to carry out this algorithm, the design component 120 may receive the set of all unique epitope sequences present in the pathogen population provided as input data, as well as weighting factors including frequencies of occurrence $f_i$ that correspond to the number of viral strains in the pathogen population include an i-th epitope sequence, from the input component 110. Based on this information, the design component 120 can then design an optimal candidate vaccine strain by finding a sequence S such that $\Sigma_{i \in s} f_i$ is a maximum. Additionally, the weighting factors received from the input component 110 and utilized by the design component 120 may include additional information, such as the probability that the received epitope sequences are MHC-I epitopes, the expressiveness of given epitope sequences, potential cross-reactivity between epitope sequences, and/or other information. This additional information can then be considered in addition to the frequencies of occurrence in optimizing a candidate sequence S.

In another example, the design component 120 may also design a vaccine composed of one or more candidate strains based on specific characteristics of a pathogen for which the vaccine is designed or a recipient to which the vaccine will be delivered. For example, the algorithm described above can be altered as necessary to construct a candidate vaccine for a pathogen or recipient in which an infected cell is not capable of processing a single candidate vaccine sequence so as to present every epitope on its surface. Additionally and/or alternatively, a candidate vaccine can be constructed to take into account cross-reactivity, the human leukocyte antigen (HLA) type of a recipient, MHC binding affinity, and/or a physics-based T-cell binding model. Further, the candidate vaccine can be constructed to mitigate problems associated with immunodominance by designing different components of the candidate vaccine for delivery in different vectors. As another example, the candidate vaccine can be designed to concentrate on a particular segment of a protein to facilitate more complete blocking of the pathways in a protein segment as opposed to partial blocking of the pathways in a full protein.

Referring now to FIG. 2, a block diagram of a system 200 that facilitates vaccine design in accordance with an aspect of the present invention is illustrated. In one example, system 200 includes a graphing component 115 that can receive a set of peptide sequences and a set of design parameters. The peptide sequences and design parameters received by the graphing component 115 may respectively correspond to epitope sequences and weighting factors provided by an input component (e.g., an input component 110) from a set of viral sequences, or alternatively the peptide sequences and design parameters can be provided directly to the graphing component 115. In accordance with one aspect, upon receiving the peptide sequences and design parameters, the graphing component 115 can construct a graph representing the received information. A graph can be constructed by the graphing component 115, for example, by creating a vertex corresponding to each unique peptide sequence received by the graphing component 115, weighing each vertex based on the received design parameters, and creating edges to connect vertices in the graph that correspond to overlapping peptide sequences. Once a graph is created by the graphing component 130, it may then be provided to the design component 130 to facilitate the construction of a candidate vaccine.

By way of specific, non-limiting example, the graphing component 115 may construct a graph based on received peptide sequences and design parameters as follows. First, the graphing component 115 may receive a set of peptide sequences corresponding to a database $X=\{x_i, i=1, \ldots, N\}$ of N epitope sequences, each having a length of 10 amino acids, which appear in the strains of a target pathogen population. Thus, each epitope can be denoted using a 10-symbol word $x_i \in \{\mathbb{A}\}^{10}$, where the symbols in $\mathbb{A}$ are drawn from the alphabet of 20 amino acids. However, while the present example describes a database X containing epitope sequences of 10 amino acids in length, it should be appreciated that epitope sequences of any length may be utilized by the graphing component 115. Further, it should be appreciated that the peptide sequences received by the graphing component 115 may include peptide sequences that are not known to be good MHC binders or otherwise not known to be epitope sequences. In one such example, the graphing component 115 can assume that all received peptide sequences are epitopes. In an alternative example, the design parameters received by the graphing component 115 can reflect the probability that each of the peptide sequences are epitopes.

After receiving a database X of epitope sequences, each epitope $x_i$ in the database X can then be weighted using scalar design parameters $w_i \in \{\mathbb{Z}^*\}$, where each design parameter $w_i$ is proportional to the frequency of occurrence of epitope $x_i$ in the observed population of strains. In one example, each epitope $x_i$ may then be further weighted using design parameters that correspond to other weighting factors. For example, the epitope sequences $x_i$ may be further weighted to reflect a case in which the epitopes are not known to be good MHC binders as described above.

Once each epitope $x_i$ is identified and weighted, the graphing component 115 can then construct a weighted epitope overlap graph $\mathcal{G}(V, W, E, L)$ to represent the epitope sequences as follows. First, a vertex $v_i \in V$ may be created for each epitope $x_i$, where V represents the set of all N vertices in $\mathcal{G}$. Next, directed edges $e_{ij}=v_i \to v_j \in E$, where E represents the set of all directed edges in $\mathcal{G}$, can be created to connect two vertices $v_i$ and $v_j$ in the graph if the epitopes $x_i$ and $x_j$ corresponding to the respective vertices overlap. In one example, only the maximum overlap for an ordered pair of epitopes may be considered by the graphing component 115 in connecting vertices in the graph $\mathcal{G}$. For example, it can be observed that two given epitopes $x_1$=PGVRYPLTFG and $x_6$=GVRYPLTFGW overlap at nine positions. By utilizing the maximum overlap of nine positions, a resulting sequence of "PGVRYPLTFGW" can be obtained. Because only the maximum overlap is considered, a resulting sequence from an inferior overlap, such as "PGVRYPLTFGVRYPLTFGW," may not be considered by the graphing component 115. Additionally, epitope overlap may be defined by the graphing component 115 as a one-way property such that inverse overlap is not considered. For example, it can be seen that an epitope sequence $x_7$=WGFTLPYRVG (i.e., a sequence composed of inversely ordered amino acids of $x_6$) exhibits inverse overlap with $x_1$. However, the graphing component 115 may nonetheless determine that $x_7$ does not overlap $x_1$, and consequently the graphing component 115 may not connect $x_7$ with $x_1$ via a directed edge from $x_7$ to $x_1$, as the groove into which said epitopes bind is not symmetric about its center.

As further used in the graph $\mathcal{G}(V, W, E, L)$, W may correspond to a set of weights $W=\{w_1, \ldots, w_N\}$ that are respectively applied to each vertex $v_i \in V$. Further, each directed edge $e_{ij}$ between vertices $v_i$ and $v_j$ may be weighted by using a parameter $l_{ij} \in \{\mathbb{Z}^*\}$ that quantifies the depth of the overlap between the corresponding epitopes $x_i$ and $x_j$. For example, an edge weight $l_{16}$, which corresponds to the overlap between $x_1$ and $x_6$, may be set equal to 9 by the graphing component 115 to reflect the fact that $x_1$ and $x_6$ overlap at 9 positions. As another example, two vertices $v_i$ and $v_j$ that are not connected may have a default edge weight $l_{ij}=0$.

In accordance with another aspect, system 200 further includes a design component 120 that can design a candidate vaccine sequence S based on the graph $\mathcal{G}(V, W, E, L)$ constructed by the graphing component 115. By way of specific, non-limiting example, the design component 120 can construct a sequence S from the graph $\mathcal{G}$ by determining a path through the graph $\mathcal{G}$ having a maximum cumulative vortex weight for a given sequence length K. Accordingly, the design component 120 can design a candidate sequence S by employing an algorithm for solving a max-weight length-constrained path (MLP) problem with respect to graph $\mathcal{G}$. In one example, this MLP problem can be expressed as follows. Given the graph $\mathcal{G}$ (V, W, E, L) from the graphing component 115, the design component 120 may construct a candidate sequence S as a subset of vertices S ⊂ V in graph $\mathcal{G}$ having a cardinality of M. The subset S may be constructed according to a permutation π: {1, . . . , M}→{1, . . . , M} of the subset S such that the length of the candidate sequence represented by subset S is equal to the given sequence length K, i.e., $$10 + \sum_{i=1}^{M-1} [10 - l_{s(\pi(i))s(\pi(i+1))}] = K.$$

Based on this construction, a subset S can then be chosen for the candidate sequence that maximizes the total vertex weight of the vertices in subset S, which may be represented as $$\lambda = \sum_{i=1}^{M} w_{s(i)}.$$

Based on this definition of the MLP problem, the design component 120 may employ various algorithms that exploit overlap among epitopes to construct a vaccine of a given length of K amino acids such that the vaccine maximizes the number of epitopes that frequently occur in the strains that compose the target pathogen population.

It should further be appreciated that the MLP problem described above for which the design component 120 employs algorithms for vaccine design is NP-complete. This may be proven, for example, as follows. First, a polynomial transformation f(): $\mathcal{G}$ (V, W, E, L)→$\mathcal{G}$'(V, Z, E, L) can be defined such that a uniform weight $w_i$=1 is set for each respective node $v_i$ϵV and a constant edge weight z(e)=1ϵZ is applied to each edge e ϵE. Based on the above transformation, a polynomial time algorithm that finds an optimum solution to the MLP problem for f($\mathcal{G}$) would also solve the equal-edge-weight variant of the longest weight-constrained path problem for $\mathcal{G}$', which has previously been proven to be NP-complete via the knapsack problem. Accordingly, it can be seen that the above MLP problem is also NP-complete.

Figure 3:
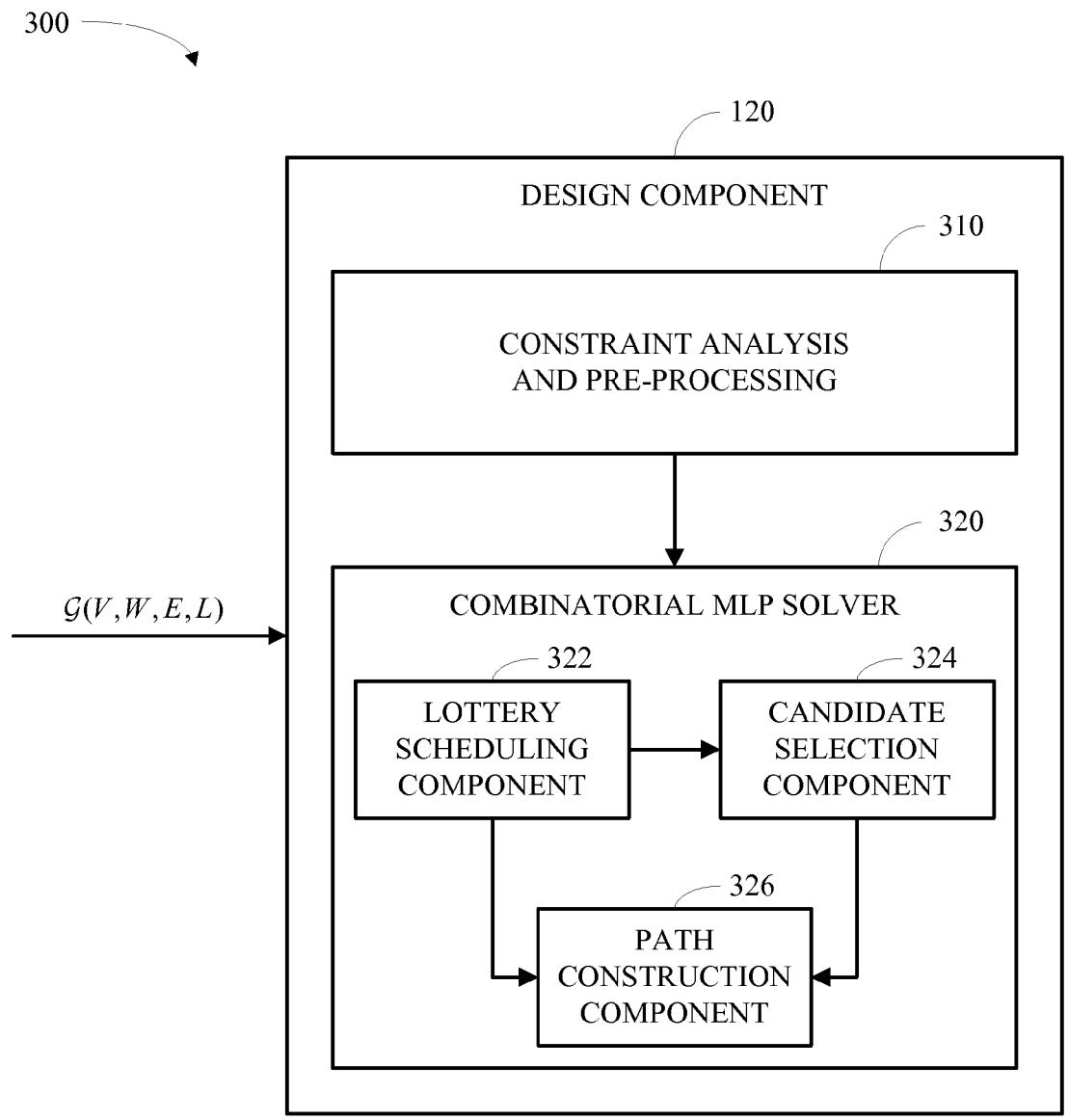
FIG. 3 is a block diagram of a system that constructs a candidate vaccine sequence using a max-weight length-constrained path algorithm in accordance with an aspect of the present invention.

Turning now to FIG. 3, a block diagram of a system 300 that constructs a candidate vaccine sequence using a MLP algorithm in accordance with an aspect of the present invention is illustrated. In one example, system 300 includes a design component 120 that may receive a graph $\mathcal{G}$ (V, W, E, L) (e.g., from a graphing component 115) that characterizes epitope sequences present in a target pathogen population and relationships therebetween in a similar manner to the design component 120 in system 200. From the graph $\mathcal{G}$ (V, W, E, L), the design component 120 may then construct a vaccine sequence S using a MLP-solving algorithm. In one example, the design component 120 may utilize a combinatorial MLP-solving approach. It should be appreciated that this is in contrast to typical MLP-solving approaches, wherein the complexity of the MLP problem is approached from the usual perspective of analyzing the best approximation algorithm.

By way of example, a combinatorial MLP-solving approach may be desirable for the design component 120 for at least the following reasons. First, while collected strain databases for rapidly mutating pathogens, such the HIV virus, may pose significant difficulty for exact solvers, many real-life instances of NP-complete problems such as the MLP problem may be significantly easier to solve near-optimally using simple heuristics. In addition, as in the case of many computational biology problems, the solution obtained by the design component 120 may be regarded as being significantly more important than the algorithm employed by the design component 120. Thus, a combinatorial approach may be employed to trade off speed for solution quality.

In accordance with one aspect, the design component can execute a combinatorial MLP algorithm by employing a combinatorial MLP solver module 320 that utilizes a simple least-constraining most-constrained probabilistic heuristic, which may be preceded by a constraint analysis and pre-processing module 310 that aims at simplifying the search space of the MLP problem. Accordingly, the MLP algorithm executed by the design component 120 may begin with the constraint analysis and pre-processing module 310 by preprocessing input epitopes from the graph $\mathcal{G}$ (V, W, E, L) in order to reduce the overall search space. In one example, two epitopes may be merged by module 310 into a longer sequence when a strong force exists for the two epitopes to appear jointly in virus strains.

By way of non-limiting example, the reduction performed by module 310 may proceed as follows. First, epitopes in a set X corresponding to the vertices V in graph $\mathcal{G}$ may be sorted in decreasing order of the function $g(x_i)=w_i/h(x_i)$, where function $h(x_i)$ returns the current length of an epitope sequence $x_i$. In the non-limiting example where each epitope sequence $x_i$ is initially 10 amino acids in length, it can be seen that prior to any pre-processing by module 310, $(\forall x_i \epsilon X)h(x_i)=10$. The resulting sorted list of sequences may then be processed starting from a vertex $x_i$ having the highest value of $g(x_i)$. Next, a group of vertices G can be determined such that $l_{ji} > \vartheta$ =const. for any $x_j \epsilon G$, and the sequence $x_j \epsilon G$ with the largest $g(x_j)$ can be identified. A second group of vertices G' can then be determined such that $l_{jk} > \vartheta$ for any $x_k \epsilon G'$, and the sequence $x_k \epsilon G'$ with the largest $g(x_k)$ can then be identified. Upon identifying the sequences $x_j$ and $x_k$, module 310 may then compare sequences $x_i$ and $x_k$. If $x_i = x_k$, module 310 may then merge $x_i$ and $x_j$ into a single epitope sequence $x_m$ of length $h(x_m)=h(x_i)+h(x_j)-l_{ij}$ and replace $x_i$ and $x_j$ in the set X with $x_m$ In one example, this procedure may then be repeated until all pairs of vertices in X that could merge according to these requirements are merged. In another example, the constant $\vartheta$ can be defined as a threshold on the overlap. The constant $\vartheta$ can be applied as a filter by module 310, for example, to avoid merging nodes having only a shallow level of overlap. This may be done to allow such vertices to instead be connected by the combinatorial MLP solver module 320 in the search phase of the algorithm employed by the design component 120.

It should be appreciated that the reduction procedure employed by module 310 may be sub-optimal for arbitrary input. Instead, it should be appreciated that the key objective of module 310 is to attach epitopes that match well in terms of depth of overlap and frequency of occurrence in a target strain population. However, experimentation has shown that the benefits of module 310, such as the reduction of |X| by approximately 7% for some test cases, can nonetheless be worthwhile considering the proximity of the obtained final solution to an optimistic upper bound.

Upon preprocessing by module 310, the MLP algorithm employed by the design component 120 in system 300 may continue to a combinatorial MLP solver module 320. In one example, module 320 can employ a probabilistic least-constraining most-constrained algorithm to find an optimal vaccine design. Under this algorithm, an optimal vaccine design can be determined from paths in graph $\mathcal{G}$ that may be randomly generated using a lottery-scheduling-based search strategy and a set of computationally inexpensive cost functions. By way of specific, non-limiting example, an algorithm that may be employed by module 320 is detailed using pseudo-code in Table 1 below:

TABLE 1

Pseudo-code for an example MLP Solver algorithm.

A Simple MLP Solver

Input: Graph G, number of search iterations L.
1  while L > 0
2    Set path $\Pi = LS(V, \phi())$.
3    while $\sum_{x \in \Pi} g(x) < K$
4      $\pi_H$ and $\pi_T$ are the head and the tail of $\Pi$.
5      Head-candidate $v_H = LS(V - \Pi, q_H(\pi_H))$.
6      Tail-candidate $v_T = LS(V - \Pi, q_T(\pi_T))$.
7      Add-on $a = LS(\{v_H, v_T\}, \{q_H(v_H, \pi_H)^3, q_T(v_T, \pi_T)^3\})$.
8      if $a = v_H$ then $\Pi = \{V_H, \Pi\}$
9      else $\Pi = \{\Pi, v_T\}$.
10   if $\lambda = \sum_{\forall v_i \in \Pi} w_i > \lambda_{max}$
11   then current best path $\Pi_{max} = \Pi$, set $\lambda_{max} = \lambda$.
12   L = L - 1.
Lottery Scheduling (LS)

Input: Set X, objective function $\alpha(): \{x \in X\} \to \mathbb{R}$
1  Compute $(\forall x_i \in X) a_i = \alpha(x_i)$
2  Generate random number r within $\left[0, \sum_{i=1}^{|X|} a_i\right]$.
3  Find j such that $\sum_{i=1}^{j} a_i \leq r < \sum_{i=1}^{j+1} a_i$.
4  return $x_j$.

In one example, lottery scheduling (LS) can be used as the fundamental selection process in the algorithm detailed in Table 1 that may be employed by module 320. Under LS, an item $x_i$ can be selected from a set of items X such that the probability the item $x_i$ will be selected is proportional to a normalized criterion function $$\alpha(x_i) \left[\sum_{\forall x \in X} \alpha(x)\right]^{-1}.$$

In another example, this selection process may be done in $\mathcal{O}(\log_2 |X|)$ by using a simple binary tree. As used herein, the LS procedure is represented by the function $LS(X, \alpha())$, which returns a member of X.

In a specific, non-limiting example, the algorithm described above in Table 1 can be performed by module 320 by creating L distinct paths over G and then choosing a path from the L created paths having the best total weight $\lambda$. A least-constraining most-constrained heuristic may be utilized by module 320 to construct each path as follows. First, a starting node in a respective path may be selected according to $$\Pi = \{v\} = LS(V, \phi()), \text{ where } \phi(v_i) \equiv \frac{w_i}{g(v_i)}.$$

Next, new nodes may be iteratively concatenated to $\Pi = \{\pi_H, \ldots, \pi_T\}$ until the length of the resulting sequence corresponding to the path is equal to or greater than a predetermined vaccine length K. In one example, each new vertex may be concatenated to the path as follows. First, for both the head $\pi_H$ and the tail $\pi_T$ of the path, concatenation candidates $v_H = LS(V-\Pi, \tilde{n}_H(\pi_H))$ and $v_T = LS(V-\Pi, \tilde{n}_T(\pi_T))$ may be computed. As used for the computation of the concatenation candidates, functions $\tilde{n}_H()$ and $\tilde{n}_T()$ may be defined as follows:

$$\tilde{n}_H(v, \pi_H) \equiv \frac{\max_{v \in V-\Pi} l_{v\pi_H} w_v}{\left[g(v) - \max_{v \in V-\Pi} l_{v\pi_H}\right]\left[1 + \max_{v \in V-\Pi} l^2_{\pi_H v}\right]}, \quad (1)$$

$$\tilde{n}_T(v, \pi_T) \equiv \frac{\max_{v \in V-\Pi} l_{\pi_T v} w_v}{\left[g(v) - \max_{v \in V-\Pi} l_{\pi_T v}\right]\left[1 + \max_{v \in V-\Pi} l^2_{v\pi_T}\right]}. \quad (2)$$

Equations (1) and (2) may be used by module 320, for example, to heuristically quantify how attracted two vertices are. It can be observed from Equations (1) and (2) that the most constrained vertices in the current remainder of nodes V−Π with high overlap at the head or the tail of Π as well as high weight may tend to increase the output of Equations (1) and (2). On the other hand, it can be observed from the second term in the denominator of Equations (1) and (2) that the cost functions represented by Equations (1) and (2) may be relaxed if a candidate vertex has a high overlap with a vertex in V−Π. Thus, by utilizing Equations (1) and (2), module 320 can choose less constraining head and tail candidates while concatenating candidate vertices. After module 320 identifies candidate vertices $v_H$ and $v_T$, a candidate vertex can be selected from $v_H$ and $v_T$ and appended to the current path Π by using an additional round of lottery scheduling, which may use a corresponding $\varrho()^3 ()^3$ function to establish the probability of occurrence.

In accordance with one aspect, the search algorithm utilized by the design component 120 in system 300 may be formulated with the objective of rapidly producing new candidate paths having a high likelihood of producing a high total weight $\lambda$. While some conventional MLP algorithms exist that may perform faster on average than the algorithm employed by the design component 120, the performance of the algorithm employed by the design component 120 has been shown to yield satisfactory performance for vaccine design applications against provided HIV strain benchmarks.

Additionally, vaccines designed by the design component 120 can be a flexible representation of HIV diversity and/or other pathogen diversity. To this end, the algorithm employed by the design component in system 300 can accommodate several extensions. For example, the vaccine model utilized by the design component 120 can be adjusted to include additional constraints that pertain to the expressiveness of epitopes in a constructed vaccine strain. More particularly, several adjustments may be readily included to adapt the vaccine model utilized by the design component 120 to various circumstances, such as a cross-reactivity submodel, a model that quantifies the uncertainty about whether a peptide sequence is an MHC-I epitope, a model that accounts for the influence of flanking regions on epitope presentation, a model that associates viral mutations with HLA types of individual vaccine recipients, a physics-based T-cell binding model, and/or other suitable adjustments. As another example, problems associated with immunodominance may be attenuated by adjusting and optimizing the design component 120 to construct a vaccine candidate that can be administered by delivering components of a cocktail in different vectors. As yet another example, the algorithm performed by the design component 120 can be adjusted to concentrate on a particular segment of a protein such that a constructed vaccine may block virtually all evolutionary pathways in a protein segment rather than blocking many but not all pathways in a full protein, which may be useful in the design of vaccines for various pathogens under certain circumstances.

Further, it should be appreciated that combinatorial optimization techniques, such as the combinatorial MLP approach utilized by the design component 120 in system 300, can be well suited to applications such as vaccine design due to their ability to explore search spaces efficiently. It can be observed from experimentation that optimal designs in such search spaces often have a certain degree of randomness associated with their structure. Accordingly, greedy heuristics guided by traditional signal processing and machine learning algorithms may be unable to find such structures. While combinatorial optimization problems can be intractable for arbitrary instances, it should be appreciated that many real-life instances can be solved optimally or near-optimally across several problem domains.

Figure 4:
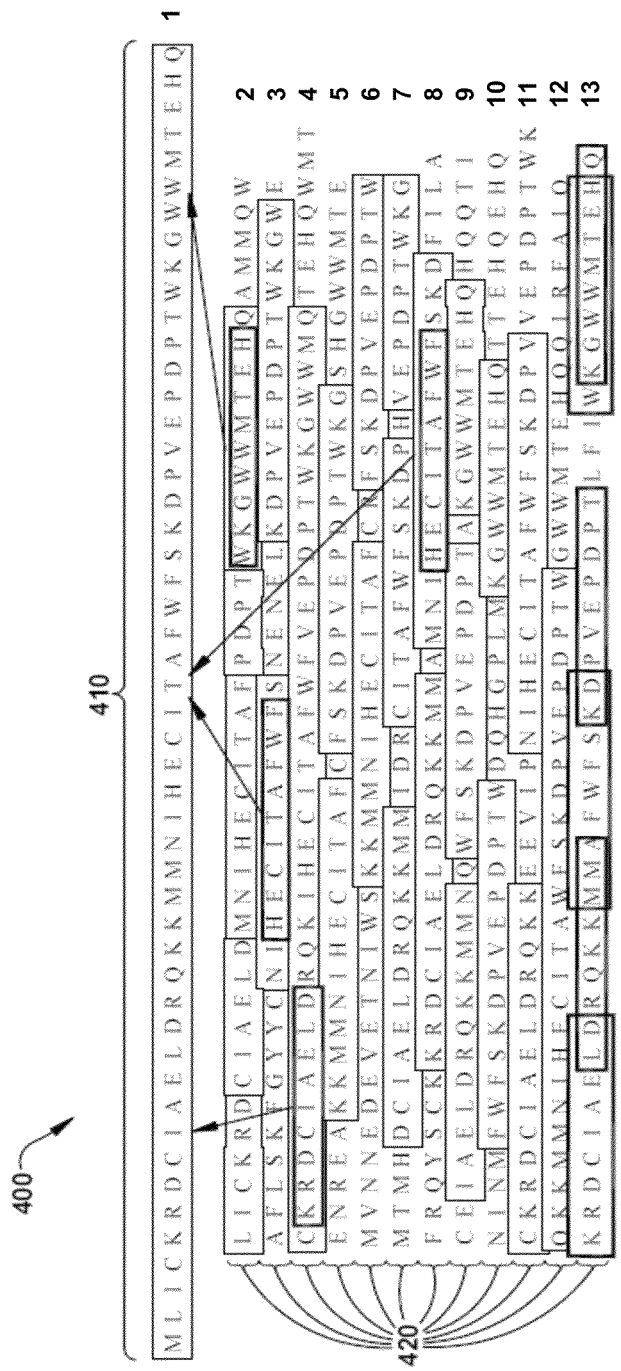
FIG. 4 is a diagram that illustrates a mapping between an epitome and amino acid sequences represented by the epitome in accordance with an aspect of the present invention.

Turning now to FIG. 4, a diagram 400 is provided that illustrates a mapping between an epitome 410 and amino acid sequences 420 represented by the epitome 410 in accordance with an aspect of the present invention. The identified row numbers and their corresponding SEQ ID NO is provided as follows: Row 1 (SEQ ID NO: 1); Row 2 (SEQ ID NO: 2); Row 3 (SEQ ID NO: 3); Row 4 (SEQ ID NO: 4); Row 5 (SEQ ID NO: 5); Row 6 (SEQ ID NO: 6); Row 7 (SEQ ID NO: 7); Row 8 (SEQ ID NO: 8); Row 9 (SEQ ID NO: 9); Row 10 (SEQ ID NO: 10); Row 11 (SEQ ID NO: 11); Row 12 (SEQ ID NO: 12); and Row 13 (SEQ ID NO: 13). In one example, the epitome 410 can characterize the amino acid sequences 420 in terms of epitopes that are subsequences of the sequences 420. One or more epitopes present in the amino acid sequences 420 may be mapped to overlapping portions of the epitome 410, thereby allowing the epitome 410 to be less than half as long as an epitome with similar coverage that does not exploit epitope overlap. Each letter illustrated in diagram 400 may correspond to one amino acid in the epitome 410 and/or amino acid sequences 420. Further, letters in diagram 400 corresponding to amino acids that are contained in at least one epitope are shaded. Selected epitopes present in the sequences 420 are also marked with boxes. Accordingly, it can be seen that epitope sequences may also overlap in the sequences 420.

Figure 5:
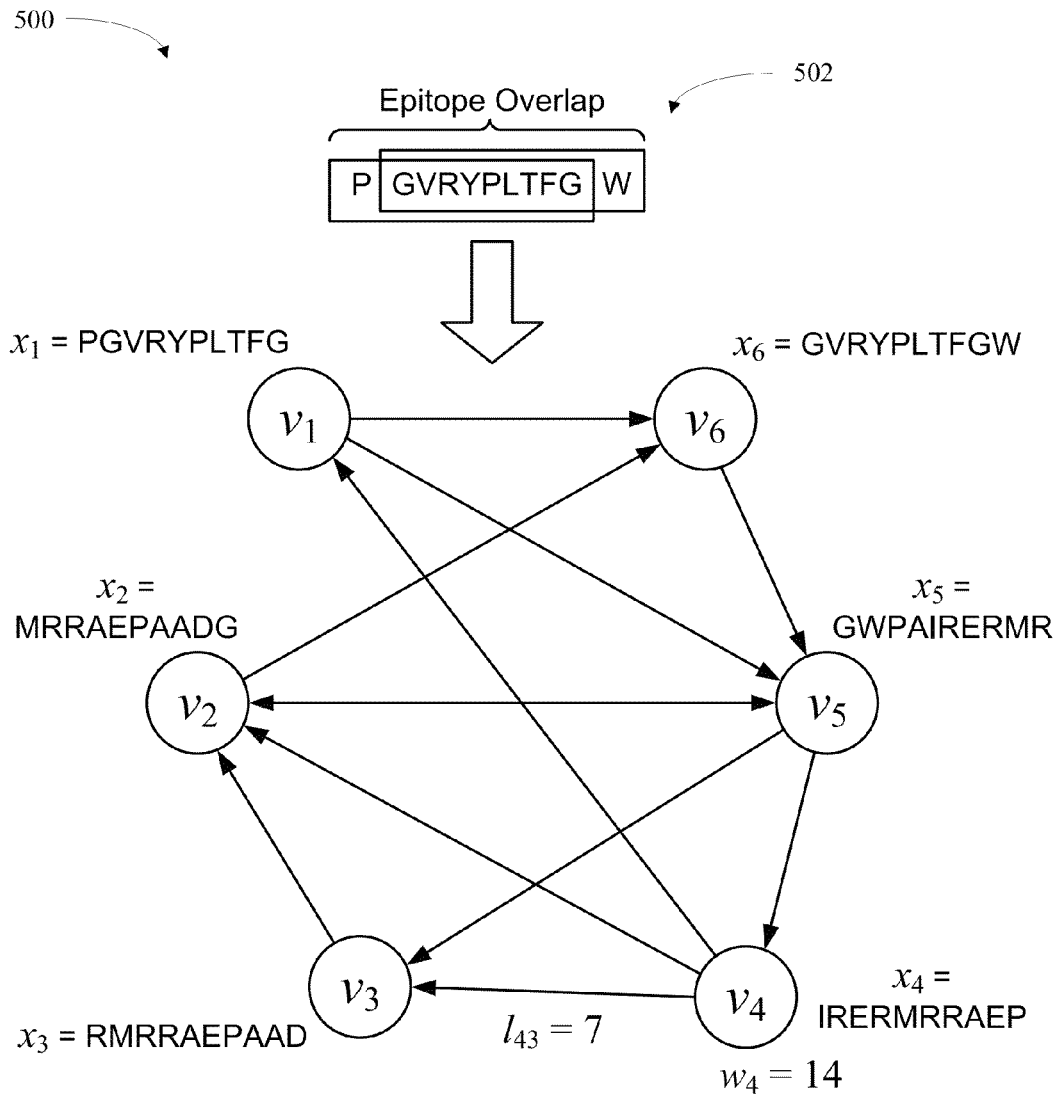
FIG. 5 illustrates an example epitope graph in accordance with an aspect of the present invention.

Referring to FIG. 5, an example epitope graph 500 in accordance with an aspect of the present invention is illustrated. Epitope graph 500 may correspond to, for example, a graph G(V, W, E, L) generated by a graphing component 115. In one example, the graph 500 can include vertices $v_i$ that correspond to respective epitope sequences $x_i$. Each vertex $v_i$ can also be assigned a weight $w_i$, which may correspond to the frequency of a corresponding epitope sequence $x_i$ in a target pathogen population and/or other appropriate factors. For example, as illustrated in graph 500, the weight $w_4$ corresponding to the vertex $v_4$ is 14. Each vertex may also be connected to other vertices via directed edges if the epitope corresponding to the vertex overlaps epitopes corresponding to other vertices. As illustrated in graph 500, as epitope overlap 502, the epitope $x_1$=PGVRYPLTFG overlaps the epitope $x_6$=GVRYPLTFGW. Thus, a directed edge may be constructed from vertex $v_1$ to vertex $v_6$. Each edge may also be given a weight that may correspond to the depth of overlap between epitopes $x_i$ and $x_j$. For example, as illustrated in graph 500, it can be seen that the epitope $x_4$=IRERMRRAEP overlaps the epitope $x_3$=RMRRAEPAAD at seven positions. Accordingly, the edge weight $l_{43}$ illustrated in graph 500 is 7. The sequences shown in FIG. 5 are all portions of SEQ ID NO: 14 with positions as follows: epitope overlap 502 (positions 1-11); sequence $x_1$ (positions 1-10); sequence $x_2$ (positions 18-27); sequence $x_3$ (positions 17-26); sequence $x_4$ (positions 13-24); sequence $x_5$ (positions 10-19); and sequence $x_6$ (positions 2-11).

Figure 6:
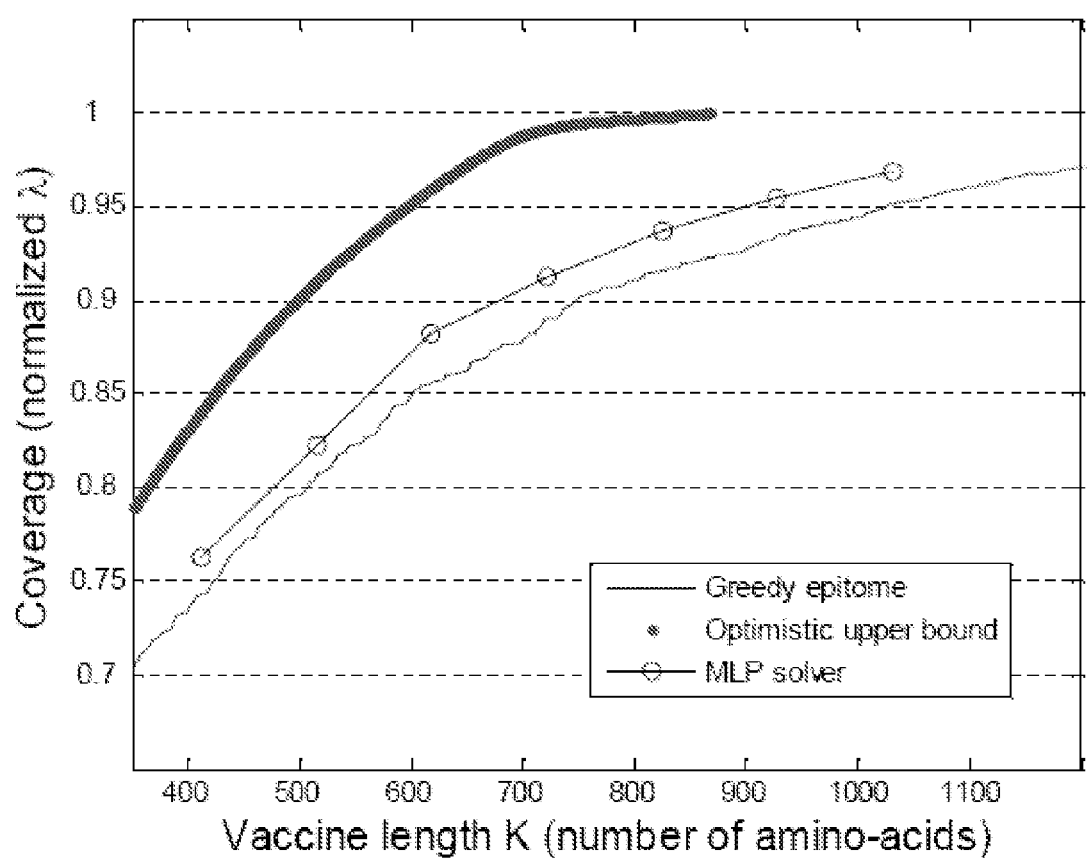
FIGS. 6-7 illustrate comparisons between performance data for example vaccine design algorithms in accordance with various aspects of the present invention and performance data for conventional vaccine design algorithms.

Turning to FIG. 6, a graph 600 is provided that illustrates a comparison between performance data for an example vaccine design algorithm in accordance with an aspect of the present invention and performance data for conventional vaccine design algorithms. To obtain the performance data illustrated in graph 600, vaccine candidates were designed for a target pathogen population consisting of 197 lade B HIV sequences taken from GenBank, each of which was obtained from a different person.

For the experimentation illustrated by graph 600, it was assumed that each subsequence of 10 amino acids from each HIV sequence, i.e., each 10-mer from the HIV sequences, is an epitope. Under these conditions, the performance of each vaccine design algorithm was measured as the coverage of all 10-mers found in the virus population. Graph 600 illustrates this performance measure as a function of vaccine length K. Three sets of results are illustrated in graph 600. One set is returned by a conventional greedy epitope design approach, which may be based on cocktails of observed strains, cocktails of consensus strains, or cocktails of tree centers. Another set corresponds to results obtained using an example MLP algorithm (e.g., an MLP algorithm executed by a design component 120) in accordance with various embodiments disclosed herein, and the third set corresponds to an optimistic upper bound. The upper bound was computed by assuming that $(\forall i \in V)(\forall j \in V, j \neq i) I_{ij} = 9$ and then taking $$\lambda^* = \sum_{v_i \in \Pi^*} w_i,$$

where $\Pi^*$ is a path created in descending order of weights in G. It should be appreciated that this upper bound is not likely to be reached by a real-life algorithm as the maximum depth of coverage (e.g., 9) between two epitopes may be achieved only for at most 20 other epitopes in a graph G.

Based on the graph 600, the improvement of the example MLP solver can be computed against the conventional approach illustrated in graph 600 by reporting $[\lambda(GE) - \lambda(MLP)][\lambda(GE) - \lambda^*]^{-1}$, where the index GE denotes results produced by the conventional greedy algorithm for epitope construction. In one example, the example MLP algorithm may achieve a 25.3% improvement over the conventional greedy epitope approach for a vaccine length K=618. It should be appreciated, however, that the results illustrated in graph 600 may not be optimal as an exact solver was not utilized for either of the K-spots due to the involved problem complexity. Alternatively, results may be reported by comparing vaccine lengths obtained using the two methods illustrated in graph 600 at an identical level of coverage. Accordingly, in order to achieve $$\lambda \left[ \sum_{v_i \in V} w_i \right]^1,$$

respective vaccine lengths of $K_{MLP}=618$ and $K_{GE}=711$ amino acids may be required. Based on these results, the example MLP algorithm may achieve an improvement of 15% over the conventional greedy epitome method. As illustrated by graph 600, it should also be appreciated that the improvement of the example MLP algorithm over the illustrated conventional approach becomes more significant as vaccine size increases. In addition, it should be appreciated that while the vaccine design problem relative to the experimentation illustrated by graph 600 was formulated to be independent of flanking regions and to assume no cross-reactivity, adjustments could be made to the problem formulation to address these constraints.

Figure 7:
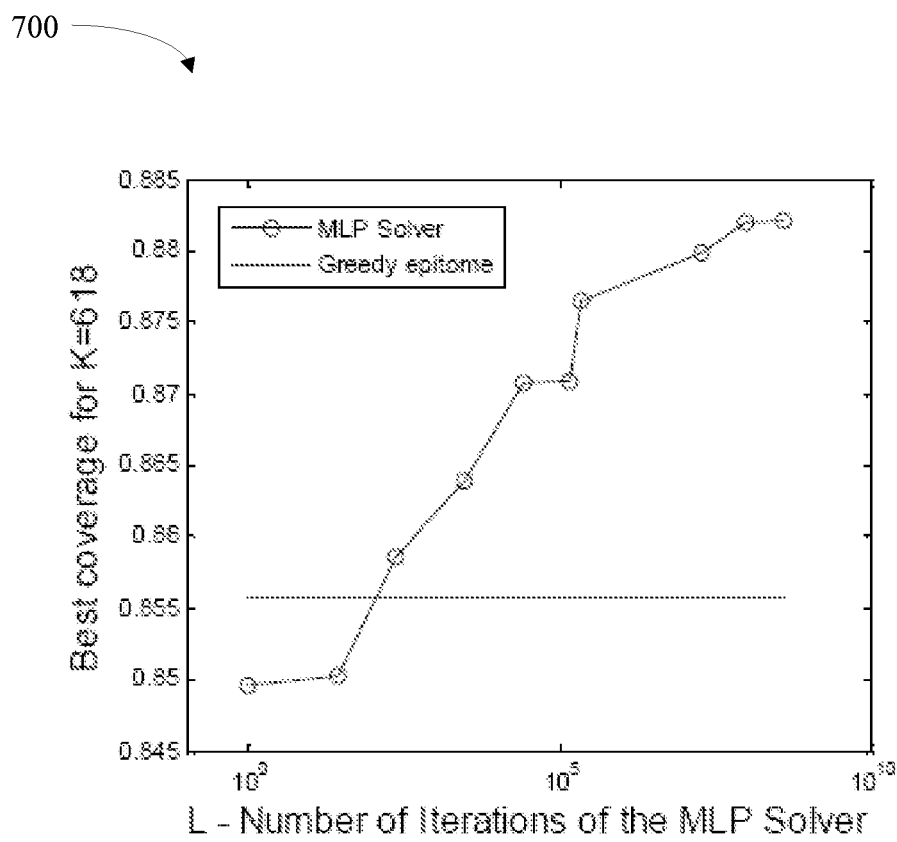

Referring now to FIG. 7, a graph 700 is provided that illustrates an additional comparison between performance data for the example MLP algorithm in accordance with various embodiments described herein and the conventional greedy epitome approach for the same target pathogen population that was used for the experimentation relative to graph 600. More particularly, graph 700 illustrates the progress of the example MLP algorithm as the number of iterations L performed by the algorithm increases. Improvement in the best result found by the example MLP algorithm for K=618 as L increases is illustrated in graph 700 and compared to the result obtained by a single iteration of the conventional greedy algorithm. During experimentation relative to graph 700, the example MLP solver was run for $L \sim 10^8$ iterations, and the moments at which the best results were obtained were computed. A 3.2 GHz Pentium machine was utilized for the experimentation, which executed iterations of the example MLP algorithm at approximately 200 paths per second. Thus, it can be observed from graph 700 that the MLP solver achieves the result obtained by the conventional greedy approach within one second of runtime.

Figures 8A, 8B:
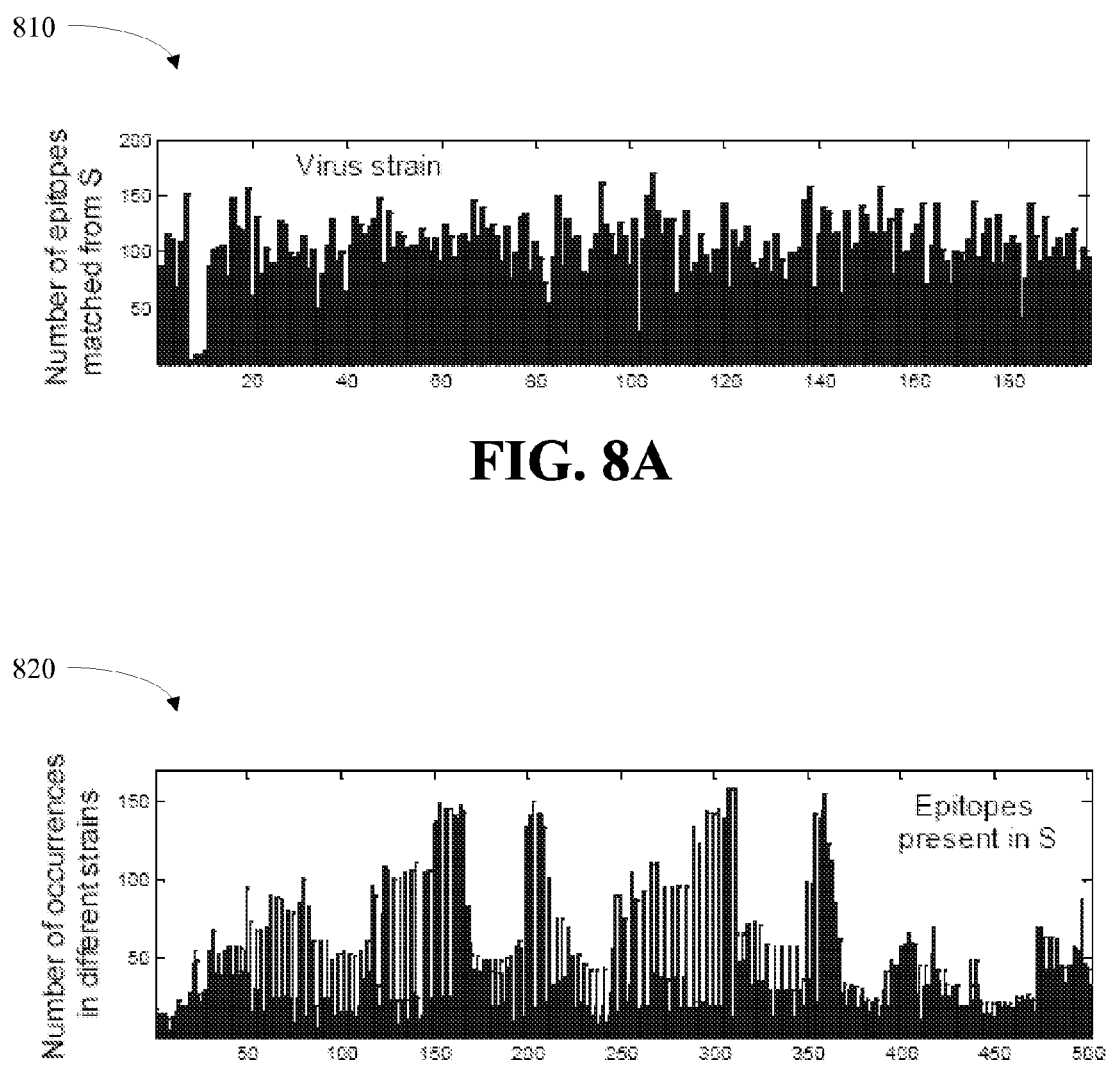

Referring to FIG. 8A, a graph 810 is provided that illustrates performance data for an example vaccine design algorithm in accordance with an aspect of the present invention. In particular, graph 810 illustrates the number of epitopes covered by a vaccine design S corresponding to a vaccine length K=618 amino acids and a normalized epitope coverage of $\lambda=0.8821$ that appear in the 197 HIV strains used for the experimentation relative to graphs 600 and 700. As can be seen from graph 810, all strains are covered by S, which points to the efficacy of the example vaccine design algorithms disclosed herein. It should be appreciated that four strains exist in the databank having indices 7-10, for which most of their genotype has not been uncovered. This explains the poor coverage illustrated by graph 810 on these strains. With respect to the other strains, a substantial portion of the strains have more than 30 containing epitopes present in the target vaccine design. In one example, the design methodology used in the experimentation relative to graph 810 could be modified by readjusting the optimization goal to provide maximum-minimum coverage of distinct strains rather than maximizing the general coverage of all strains.

Referring now briefly to FIG. 8B, a graph 820 is provided that illustrates the number of occurrences of each epitope present in the vaccine design S in distinct virus strains. Similar to graph 810, a vaccine design S having a length of K=618 is used to present the data in graph 820. As can be seen from graph 820, the resulting vaccine covered 501 out of 860 identified epitopes in the HIV strains. Additionally, it can be seen from graph 820 that many epitopes appeared in a significant portion of the individual strains.

Figure 9:
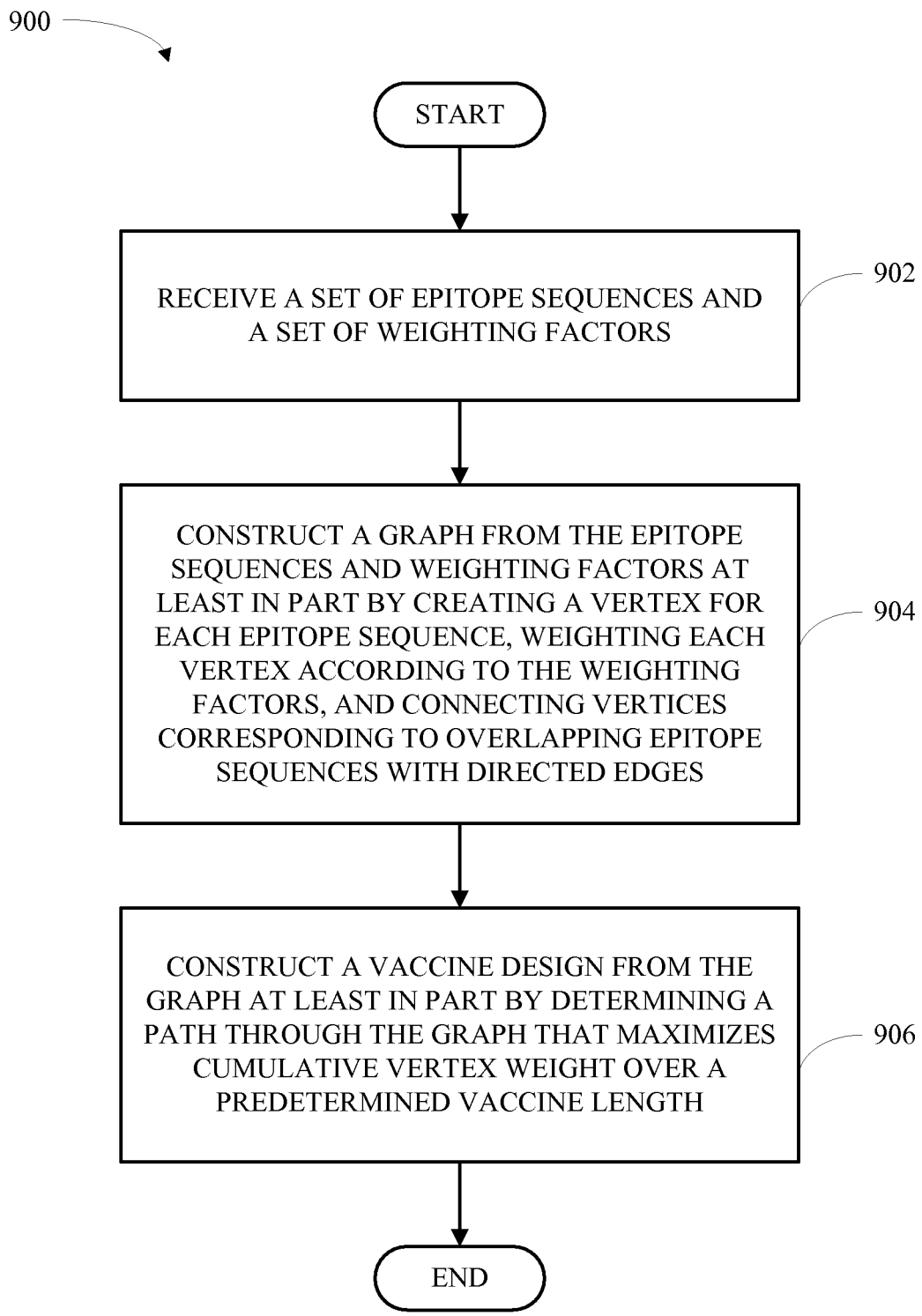
FIG. 9 is a flowchart of a method of efficient vaccine design in accordance with an aspect of the present invention.
Figure 10:
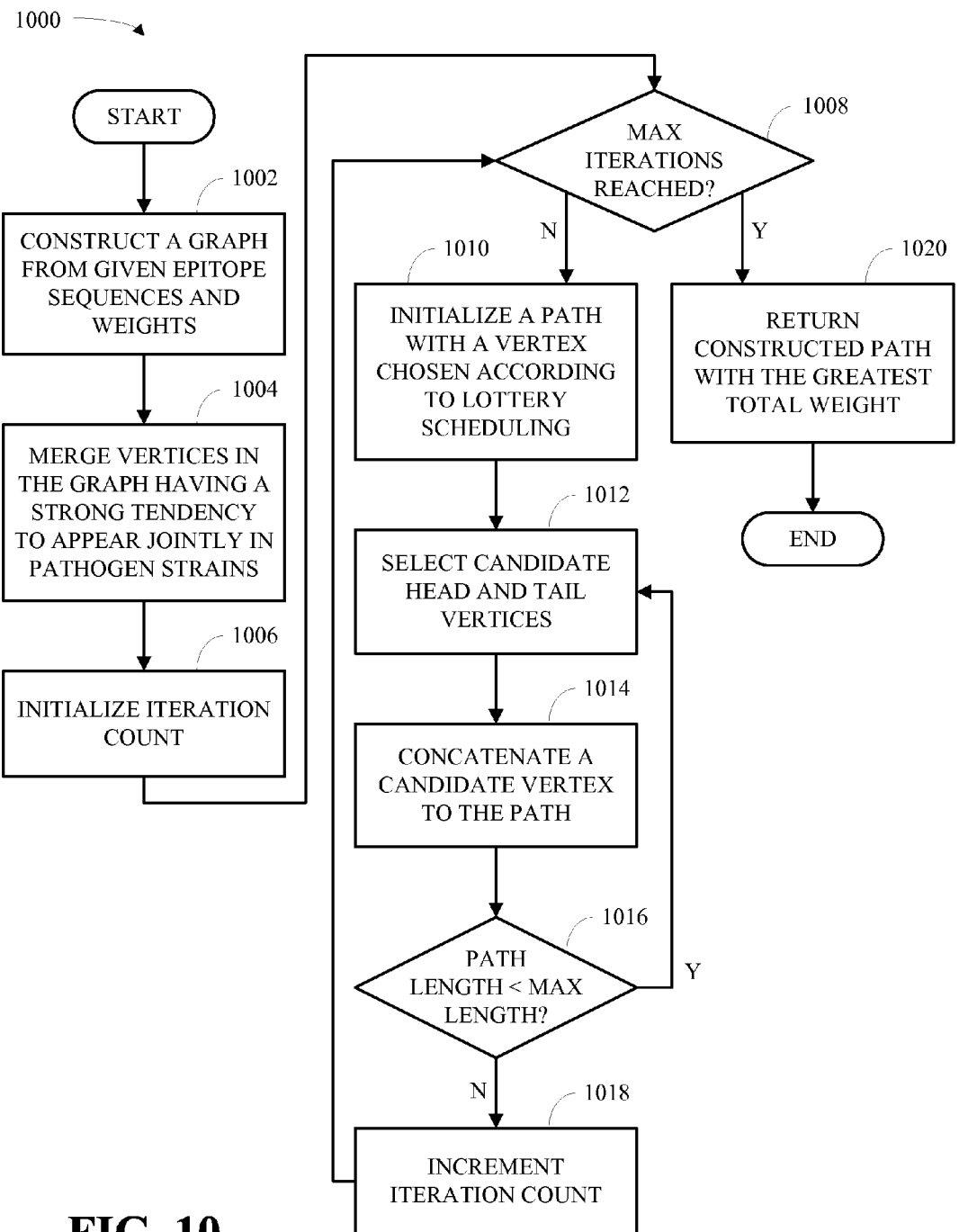
FIG. 10 is a flowchart of a method of efficient vaccine design using a max-weight length-constrained path algorithm in accordance with an aspect of the present invention.

Turning to FIGS. 9-10, methodologies that may be implemented in accordance with the present invention are illustrated. While, for purposes of simplicity of explanation, the methodologies are shown and described as a series of blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement the methodologies in accordance with the present invention.

The invention may be described in the general context of computer-executable instructions, such as program modules, executed by one or more components. Generally, program modules include routines, programs, objects, data structures, etc., that perform particular tasks or implement particular abstract data types. Typically, the functionality of the program modules may be combined or distributed as desired in various embodiments. As will be appreciated, various portions of the disclosed systems above and methods below may include or consist of artificial intelligence or knowledge or rule based components, sub-components, processes, means, methodologies, or mechanisms (e.g., support vector machines, neural networks, expert systems, Bayesian belief networks, fuzzy logic, data fusion engines, classifiers, etc.). Such components can automate certain mechanisms or processes performed thereby to make portions of the systems and methods more adaptive as well as efficient and intelligent.

Referring briefly to FIG. 9, a flowchart of a method 900 of efficient vaccine design in accordance with an aspect of the present invention is illustrated. At 902, a set of epitope sequences and a set of weighting factors are received (e.g., from an input component 110). At 904, a graph is constructed from the epitope sequences and the weighting factors (e.g., by a graphing component 115) at least in part by creating a vertex for each epitope sequence, weighting each vertex according to the weighting factors, and connecting vertices corresponding to overlapping epitope sequences with directed edges. At 906, a vaccine design is constructed from the graph (e.g., by a design component 120) at least in part by determining a path through the graph that maximizes cumulative vertex weight over a predetermined vaccine length.

Referring to FIG. 10, a flowchart of a method 1000 of efficient vaccine design using a max-weight length-constrained path algorithm in accordance with an aspect of the present invention is illustrated. Method 1000 may begin at 1002, wherein a graph (e.g. a graph $\mathcal{G}$ (V, W, E, L)) is constructed from given epitope sequences and weights (e.g., by a graphing component 115). At 1004, vertices in the graph (e.g., vertices $v_i \in V$) corresponding to epitopes having a strong tendency to appear jointly in pathogen strains may be merged (e.g. by a constraint analysis and pre-processing module 310 at a design component 120). At 1006, an iteration count may then be initialized (e.g. by a combinatorial MLP solver module 320) to facilitate the creation of a predetermined number of random paths at 1010-1016 through the graph constructed at 1002.

Each path may then be constructed as follows. At 1008, it is determined whether the maximum number of iterations has been reached, i.e., whether the predetermined number of paths have been created. If the maximum number of iterations has not been reached, method proceeds to 1010, wherein a new path is initialized with a vertex chosen according to lottery scheduling (e.g. lottery scheduling performed by a lottery scheduling component 322). At 1012, candidate head and tail vertices for the path may then be selected (e.g. by a candidate selection component 324). At 1014, one of the candidate head and tail vertices may be concatenated to the path (e.g., by a path construction component 326). At 1016, it is then determined whether the length of the path has reached a maximum vaccine sequence length. If the path length has reached the maximum vaccine sequence length, method 1000 proceeds to 1018 wherein the iteration count is incremented and then returns to 1008 wherein it is determined whether another path is to be constructed according to 1010-1016. If the path length has not reached the maximum vaccine sequence, method returns to 1012 to concatenate another vertex to the path according to 1012-1014.

Once the iteration count is incremented 1018 to be equal to the maximum number of iterations, the predetermined number of paths has been constructed and a positive determination may be made at 1008. Based on this positive determination at 1008, method 1000 may conclude at 1020, wherein the path constructed during the iterations of 1010-1016 having the greatest total weight is returned. In one example, the path returned at 1020 can correspond to an optimal vaccine sequence.

Figure 11:
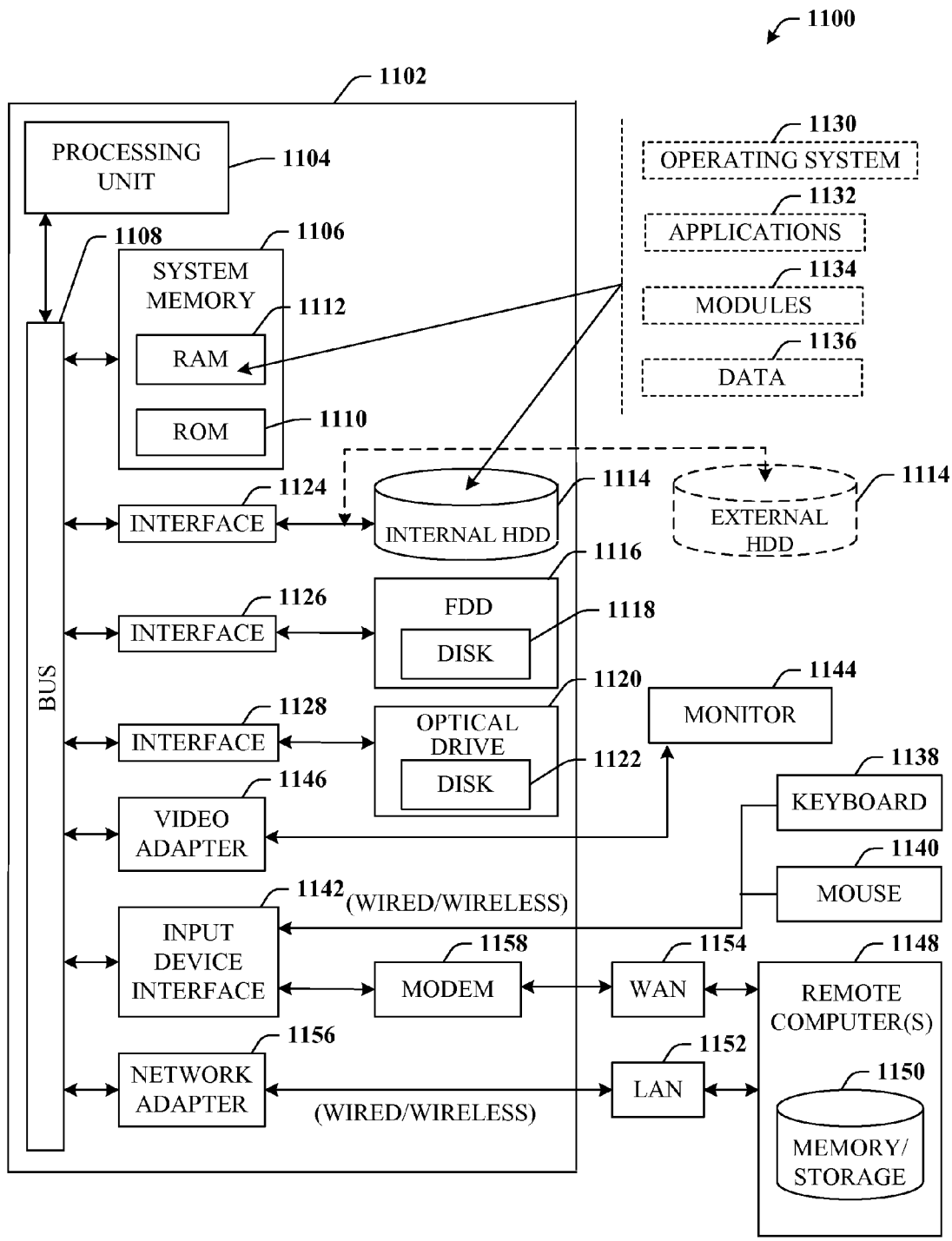
FIG. 11 is a diagram of an exemplary computing environment in which various embodiments disclosed herein may function.

In order to provide additional context for various aspects of the subject invention, FIG. 11 and the following discussion are intended to provide a brief, general description of a suitable computing environment 1100 in which the various aspects of the invention can be implemented. Additionally, while the invention has been described above in the general context of computer-executable instructions that may run on one or more computers, those skilled in the art will recognize that the invention also can be implemented in combination with other program modules and/or as a combination of hardware and software. Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, as well as personal computers, hand-held computing devices, microprocessor-based or programmable consumer electronics, and the like, each of which can be operatively coupled to one or more associated devices. The illustrated aspects of the invention may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media can include both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 11, the example computing environment 1100 includes a computer 1102, the computer 1102 including a processing unit 1104, a system memory 1106 and a system bus 1108. The system bus 1108 couples to system components including, but not limited to, the system memory 1106 to the processing unit 1104. The processing unit 1104 can be any of various commercially available processors. Dual microprocessors and other multi-processor architectures may also be employed as the processing unit 1104.

The system bus 1108 can be any of several types of bus structure that may further interconnect to a memory bus (with or without a memory controller), a peripheral bus, and a local bus using any of a variety of commercially available bus architectures. The system memory 1106 includes read-only memory (ROM) 1110 and random access memory (RAM) 1112. A basic input/output system (BIOS) is stored in a non-volatile memory 1110 such as ROM, EPROM, EEPROM, which BIOS contains the basic routines that help to transfer information between elements within the computer 1102, such as during start-up. The RAM 1112 can also include a high-speed RAM such as static RAM for caching data.

The computer 1102 further includes an internal hard disk drive (HDD) 1114 (e.g., EIDE, SATA) that may also be configured for external use in a suitable chassis (not shown), a magnetic floppy disk drive (FDD) 1116, (e.g., to read from or write to a removable diskette 1118) and an optical disk drive 1120, (e.g., reading a CD-ROM disk 1122 or, to read from or write to other high capacity optical media such as the DVD). The hard disk drive 1114, magnetic disk drive 1116 and optical disk drive 1120 can be connected to the system bus 1108 by a hard disk drive interface 1124, a magnetic disk drive interface 1126 and an optical drive interface 1128, respectively. The interface 1124 for external drive implementations includes at least one or both of Universal Serial Bus (USB) and IEEE-13114 interface technologies. Other external drive connection technologies are within contemplation of the subject invention.

The drives and their associated computer-readable media provide nonvolatile storage of data, data structures, computer-executable instructions, and so forth. For the computer 1102, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. It is appreciated that the invention can be implemented with various commercially available operating systems or combinations of operating systems.

A user can enter commands and information into the computer 1102 through one or more wired/wireless input devices, e.g. a keyboard 1138 and a pointing device, such as a mouse 1140. Other input devices (not shown) may include a microphone, an IR remote control, a joystick, a game pad, a stylus pen, touch screen, or the like. These and other input devices are often connected to the processing unit 1104 through an input device interface 1142 that is coupled to the system bus 1108, but can be connected by other interfaces, such as a parallel port, a serial port, an IEEE-1394 port, a game port, a USB port, an IR interface, etc.

A monitor 1144 or other type of display device is also connected to the system bus 1108 via an interface, such as a video adapter 1146. In addition to the monitor 1144, a computer typically includes other peripheral output devices (not shown), such as speakers, printers, etc.

The computer 1102 may operate in a networked environment using logical connections via wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wired/wireless connectivity to a local area network (LAN) 1152 and/or larger networks, e.g., a wide area network (WAN) 1154. Such LAN and WAN networking environments are commonplace in offices and companies, and facilitate enterprise-wide computer networks, such as intranets, all of which may connect to a global communications network, e.g., the Internet.

When used in a LAN networking environment, the computer 1102 is connected to the local network 1152 through a wired and/or wireless communication network interface or adapter 1156. The adapter 1156 may facilitate wired or wireless communication to the LAN 1152, which may also include a wireless access point disposed thereon for communicating with the wireless adapter 1156.

When used in a WAN networking environment, the computer 1102 can include a modem 1158, or is connected to a communications server on the WAN 1154, or has other means for establishing communications over the WAN 1154, such as by way of the Internet. The modem 1158, which can be internal or external and a wired or wireless device, is connected to the system bus 1108 via the serial port interface 1142. In a networked environment, program modules depicted relative to the computer 1102, or portions thereof, can be stored in the remote memory/storage device 1150. It will be appreciated that the network connections shown are exemplary and other means of establishing a communications link between the computers can be used.

The computer 1102 is operable to communicate with any wireless devices or entities operatively disposed in wireless communication, e.g., a printer, scanner, desktop and/or portable computer, portable data assistant, communications satellite, telephone, etc. This includes at least Wi-Fi and Bluetooth™ wireless technologies. Thus, the communication can be a predefined structure as with a conventional network or simply an ad hoc communication between at least two devices.

Wi-Fi, or Wireless Fidelity, is a wireless technology similar to that used in a cell phone that enables a device to send and receive data anywhere within the range of a base station. Wi-Fi networks use IEEE-802.11 (a, b, g, etc.) radio technologies to provide secure, reliable, and fast wireless connectivity. A Wi-Fi network can be used to connect computers to each other, to the Internet, and to wired networks (which use IEEE-802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band). Thus, networks using Wi-Fi wireless technology can provide real-world performance similar to a 10 BaseT wired Ethernet network.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

Furthermore, the aforementioned systems have been described with respect to interaction between several components. It can be appreciated that such systems and components can include those components or specified sub-components, some of the specified components or sub-components, and/or additional components, according to various permutations and combinations of the foregoing. Sub-components can also be implemented as components communicatively coupled to other components rather than included within parent components, e.g., according to a hierarchical arrangement. Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

What is claimed is:

1. A system for designing a vaccine for a pathogen population, comprising:
   a processor;
   a computer memory having stored thereon the following components executable by the processor:
   a graphing component that receives a set of epitopes present in the pathogen population and a set of weighting factors and constructs a graph at least in part by generating vertices corresponding to respective epitopes, weighting respective vertices based on one or more of the weighting factors, and generating respective directed edges between a first vertex corresponding to a first epitope and a second vertex corresponding to a second epitope that the first epitope overlaps; and
   a design component that designs a candidate vaccine sequence for the pathogen population based at least in part on a combinatorial algorithm, the candidate vaccine sequence includes overlapping epitopes corresponding to a maximum-weight length-constrained path (MLP) through the graph.

2. The system of claim 1, wherein the design component comprises a combinatorial MLP solver module that generates a predetermined number of random paths and identifies a random path that maximizes cumulative vertex weight, the random paths include vertices connected by directed edges that correspond to a sequence having a predetermined length composed of overlapping epitopes.

3. The system of claim 2, wherein the combinatorial MLP solver module comprises a path construction component that selects an initial vertex in the graph for a respective path and concatenates respective vertices to one of the head and the tail of the respective path until a predetermined sequence length corresponding to the vertices of the respective random path has been reached.

4. The system of claim 3, wherein the combinatorial MLP solver module further comprises a candidate selection component that selects a candidate head vertex and a candidate tail vertex for a respective random path and the path construction component selects a respective vertex for concatenation to the respective random path from the candidate head vertex and the candidate tail vertex.

5. The system of claim 1, wherein the design component further comprises a constraint analysis and pre-processing module that merges respective vertices in the graph corresponding to epitopes having a strong tendency to appear jointly in the pathogen population.

6. The system of claim 1, further comprising an input component that identifies the set of epitopes and the set of weighting factors from a plurality of pathogen strains in the pathogen population.

7. The system of claim 1, wherein the weighting factors include a frequency with which a respective epitope appears in the pathogen population.

8. The system of claim 1, wherein the weighting factors include one or more of a probability that a respective epitope will induce major histocompatibility complex (MHC) binding, the expressiveness of a respective epitope in a vaccine sequence, or a probability that a vaccine sequence including a respective epitope will cause cross-reactivity.

9. The system of claim 1, wherein the vaccine candidate designed by the design component is adjusted to preferentially block evolutionary pathways in a given protein segment.

10. The system of claim 1, wherein the vaccine candidate designed by the design component is optimized for delivery in multiple vectors.

11. A computer-implemented method of efficient vaccine design, comprising:
receiving a graph having vertices corresponding to epitope sequences present in the pathogen population, weights for respective vertices corresponding to respective frequencies with which corresponding epitope sequences appear in the pathogen population, and directed edges that connect vertices that correspond to overlapping epitope sequences; and
determining, by a processor, a candidate vaccine sequence of overlapping epitope sequences by identifying a path though the graph corresponding to a series of connected vertices and directed edges that maximizes the total weight of the vertices in the path for a desired vaccine sequence length.

12. The method of claim 11, wherein the graph further includes edge weights for respective directed edges based on the depth of overlap between epitope sequences corresponding to vertices that are connected by a respective directed edge.

13. The method of claim 11, wherein the graph includes one or more vertices corresponding to merged epitope sequences having a tendency to appear jointly in the pathogen population that is greater than a predetermined threshold.

14. The method of claim 11, wherein the determining a candidate vaccine sequence includes generating a predetermined number of paths through the graph and selecting a candidate vaccine sequence corresponding to a generated path having a maximum total vertex weight.

15. The method of claim 14, wherein generating a respective path through the graph includes:
selecting an initial vertex in the graph based at least in part on a lottery scheduling algorithm;
selecting a head candidate vertex to which the initial vertex is connected based at least in part on a lottery scheduling algorithm;
selecting a tail candidate vertex connected to the initial vertex based at least in part on a lottery scheduling algorithm; and
concatenating one of the head candidate vertex or the tail candidate vertex to the initial vertex to generate the respective path comprising a head vertex and a tail vertex.

16. The method of claim 15, wherein the generating a respective path through the graph further includes:
selecting a head candidate vertex to which the head vertex of the respective path is connected based at least in part on a lottery scheduling algorithm;
selecting a tail candidate vertex connected to the tail vertex of the respective path based at least in part on a lottery scheduling algorithm; and
concatenating one of the head candidate vertex or the tail candidate vertex to the respective path;
wherein the selecting a head candidate vertex, the selecting a tail candidate vertex, and the concatenating are performed iteratively until a candidate vaccine sequence corresponding to overlapping epitopes represented by the vertices of the respective path reaches a predetermined length.

17. The method of claim 15, wherein the selecting a head candidate vertex, $\tilde{n}_H(\ )$, is based on the following equation:

$$\tilde{n}_H(v, \pi_H) \equiv \frac{\max_{v \in V-\Pi} l_{v\pi_H} w_v}{[g(v) - \max_{v \in V-\Pi} l_{v\pi_H}][1 + \max_{v \in V-\Pi} l^2_{\pi_H v}]},$$

and the selecting a tail candidate vertex, $\tilde{n}_T(\ )$, is based on the following equation:

$$\tilde{n}_T(v, \pi_T) \equiv \frac{\max_{v \in V-\Pi} l_{\pi_T v} w_v}{[g(v) - \max_{v \in V-\Pi} l_{\pi_T v}][1 + \max_{v \in V-\Pi} l^2_{v\pi_T}]},$$

where V represents all vertices in the graph,
v represents a vertex,
l represents a depth of overlap,
w represents a weight,
Π represents vertices in the respective path,
$\pi_H$ represents the head of respective path,
$\pi_T$ represents the tail of respective path, and
g(v) is a function of the weight of a vertex divided by the length of its corresponding epitope sequence.

18. The method of claim 14, wherein generating a predetermined number of paths includes recording an optimal path having a maximum total vertex weight after the generation of each respective path, and the selecting a candidate vaccine sequence includes selecting a candidate vaccine sequence corresponding to the recorded optimal path.

19. A system that facilitates efficient vaccine design, comprising:
a processor
a computer memory having stored thereon the following components executable by the processor:
an input component configured to identify respective epitope sequences in a pathogen population;
a graphing component configured to generate a graph of the respective epitope sequences identified by the input component by weighting the respective epitope sequences at least in part by the frequency with which the respective epitope sequences appear in the pathogen population; and
a design component configured to design a candidate vaccine sequence having a given length by constructing a string of overlapping epitope sequences such that the total weight of the epitope sequences is maximized for the given length of the vaccine sequence.

20. The system of claim 19, wherein the design component is further configured to design a candidate vaccine sequence by constructing a plurality of strings of overlapping epitope sequences and selecting the constructed string having the highest total weight.

* * * * *